(12) United States Patent
Charlton

(10) Patent No.: US 7,393,697 B2
(45) Date of Patent: Jul. 1, 2008

(54) DIAGNOSTIC TEST FOR ANALYTES IN A SAMPLE

(75) Inventor: David Charlton, Sunnyvale, CA (US)

(73) Assignee: Advantage Diagnostics Corporation, Sunnyvale, CT (US)

( * ) Notice: Subject to any disclaimer, the term of this patent is extended or adjusted under 35 U.S.C. 154(b) by 624 days.

(21) Appl. No.: 10/456,771

(22) Filed: Jun. 6, 2003

(65) Prior Publication Data

US 2004/0248322 A1 Dec. 9, 2004

(51) Int. Cl.
G01N 33/53 (2006.01)

(52) U.S. Cl. .................. 436/518; 435/971; 435/973; 435/805; 435/287.1; 436/514; 436/513; 436/523; 436/533; 436/828; 422/56

(58) Field of Classification Search .......... 435/5, 435/7.92, 7.94, 7.95, 971, 973, 805; 436/513, 436/518, 523, 533, 828; 422/56
See application file for complete search history.

(56) References Cited

U.S. PATENT DOCUMENTS

| | | | |
|---|---|---|---|
| 4,168,146 A | 9/1979 | Grubb et al. | |
| 4,703,017 A | 10/1987 | Campbell et al. | |
| 4,857,453 A | 8/1989 | Ullman et al. | |
| 4,861,711 A | 8/1989 | Friesen et al. | |
| 5,559,041 A * | 9/1996 | Kang et al. | 436/518 |
| 5,561,045 A * | 10/1996 | Dorval et al. | 435/5 |
| 5,656,503 A | 8/1997 | May et al. | |
| 5,658,801 A * | 8/1997 | Poissant et al. | 436/518 |
| 5,714,389 A | 2/1998 | Charlton et al. | |
| 5,753,517 A | 5/1998 | Brooks et al. | |
| 5,770,458 A | 6/1998 | Klimov et al. | |
| 5,770,460 A | 6/1998 | Pawlak et al. | |
| 5,989,921 A | 11/1999 | Charlton et al. | |
| 6,027,943 A | 2/2000 | Kang | |
| 6,168,956 B1 | 1/2001 | Chandler | |
| 6,372,516 B1 | 4/2002 | Sun | |
| 6,485,982 B1 | 11/2002 | Charlton | |
| 6,492,127 B2 | 12/2002 | Goodell et al. | |
| 6,528,323 B1 | 3/2003 | Thayer et al. | |
| 6,653,066 B1 * | 11/2003 | Krutzik | 435/5 |
| 2001/0008774 A1 | 7/2001 | May et al. | |
| 2001/0023076 A1 | 9/2001 | Guan et al. | |
| 2001/0041368 A1 | 11/2001 | May et al. | |

(Continued)

FOREIGN PATENT DOCUMENTS

EP 0262328 4/1988

(Continued)

*Primary Examiner*—Bao-Thuy L. Nguyen
(74) *Attorney, Agent, or Firm*—Wilson Sonsini Goodrich & Rosati

(57) ABSTRACT

Diagnostic devices and methods are provided. The diagnostic devices preferably comprise a test strip with a test area. The sample to be analyzed contacts the test area, which comprises a specific binding partner for the analyte of interest. Analyte, if present in the sample, binds to the immobilized binding partner in the test area and is subsequently contacted with a conjugate. The conjugate specifically binds the analyte and provides a visual indication of the presence of the analyte. The devices may be used for the diagnosis of particular diseases or disorders in a patient, such as HIV or hepatitis. They may also be used to determine if an individual is pregnant.

11 Claims, 6 Drawing Sheets

U.S. PATENT DOCUMENTS

| | | |
|---|---|---|
| 2002/0045195 A1 | 4/2002 | Hubscher et al. |
| 2002/0168782 A1 | 11/2002 | McCall et al. |
| 2003/0143639 A1 | 7/2003 | Matsushita et al. |

FOREIGN PATENT DOCUMENTS

| | | |
|---|---|---|
| EP | 0291176 | 11/1988 |
| EP | 0296298 B1 | 12/1988 |
| EP | 0306336 | 3/1989 |
| EP | 0512390 | 11/1992 |
| EP | 0296398 B1 | 3/1993 |
| EP | 0973034 A1 | 1/2000 |
| WO | WO 95/13542 A1 | 5/1995 |
| WO | WO 00/07015 | 2/2000 |
| WO | WO 00/20866 | 4/2000 |
| WO | WO 00/42434 A1 | 7/2000 |
| WO | WO 01/36974 A1 | 5/2001 |

\* cited by examiner

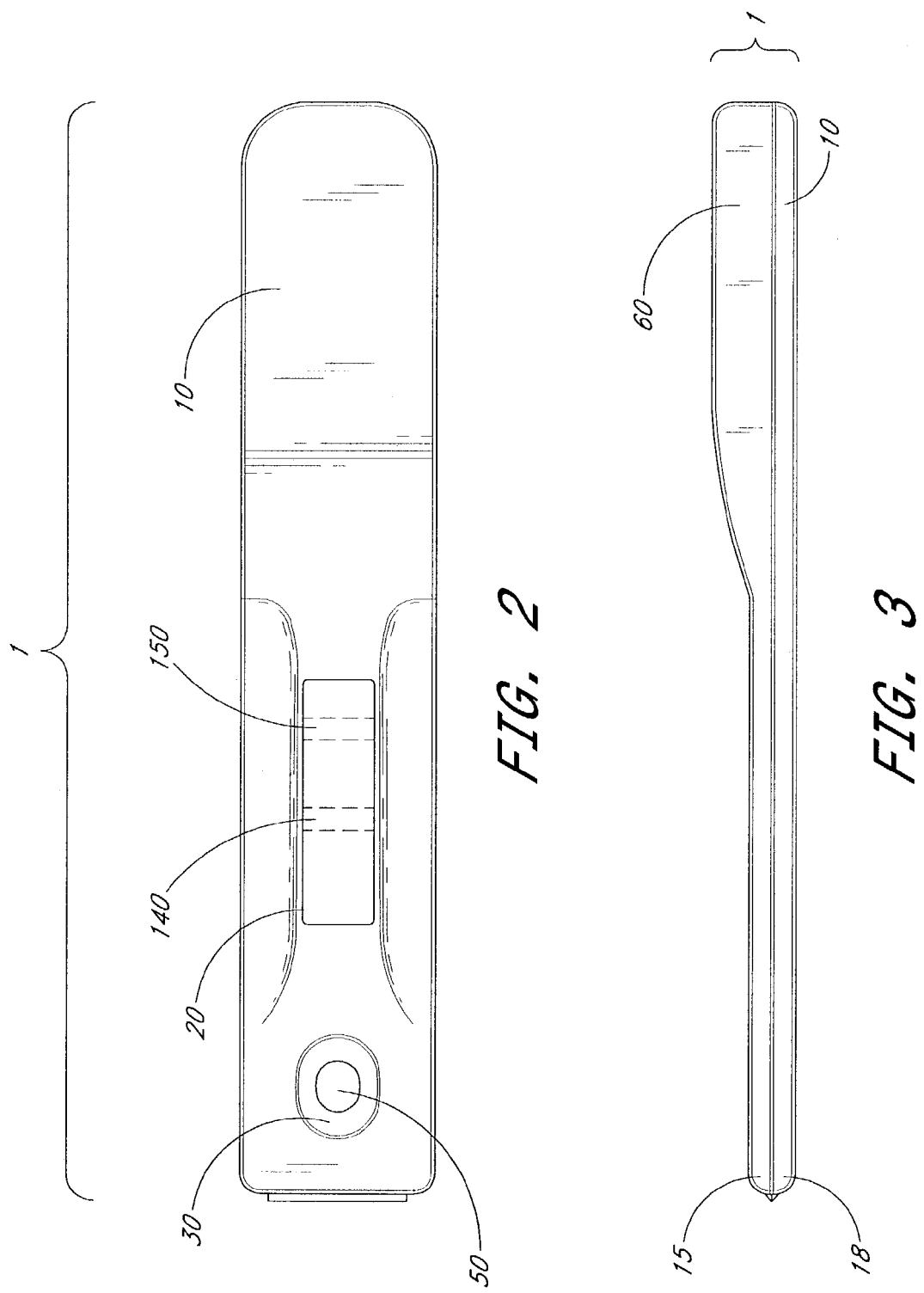

DIAGNOSTIC TEST FOR ANALYTES IN A SAMPLE

BACKGROUND OF THE INVENTION

1. Field of the Invention

The present invention relates to lateral flow rapid visual test for the detection of analytes in a sample.

2. Description of the Related Art

Lateral flow testing devices are known in the art and may be used in clinical diagnosis to determine the presence of an analyte of interest in a sample, such as a bodily fluid. However, such devices have typically required a relatively large sample volume and large amounts of conjugate. They have also had a long wait time before the results of the test can be read.

SUMMARY OF THE INVENTION

In one aspect, an immunodiagnostic test strip is provided for the detection of an analyte of interest in a sample. In some embodiments, the analyte is an antibody, such as an anti-human immunodeficiency virus (HIV) antibody or an anti-hepatitis C virus (HCV) antibody. In other embodiments the analyte is an antigen, such as human chorionic gonadotropin (hCG).

The diagnostic test strip preferably comprises a conjugate source area comprising a conjugate configured to bind the analyte of interest, a sample application area located downstream of the conjugate source area and configured to receive said liquid sample and a test area. The test area is located downstream of the conjugate source area and comprises an immobilized binding agent that is capable of specific binding to the analyte of interest. For example, if the analyte of interest is an antibody, the positive test area preferably comprises immobilized antigen. If the analyte of interest is an antigen, the positive test area preferably comprises immobilized antibody. The conjugate comprises a first binding component that is able to bind the analyte of interest and a second visualization component.

The sample used in the test may be any liquid. Preferred samples include, for example, blood, serum, plasma, saliva and urine. The sample is applied to the positive test area and conjugate is subsequently caused to flow from the conjugate source area. The conjugate flows across the membrane and contacts any analyte bound to the positive test area, producing a visual signal.

In a preferred embodiment, the test strip comprises a test area with immobilized HIV antigen and is used for the detection of anti-HIV antibodies. In this embodiment, the test is useful for the diagnosis of HIV infection in a patient. In another preferred embodiment the test strip comprises a test area with immobilized HCV antigen and is used for the detection of anti-HCV antibodies in a sample. In this embodiment the test is useful for the diagnosis of HCV infection in a patient. In a further embodiment the test strip comprises a test area with immobilized anti-hCG antibodies. In this embodiment, the test is useful for determining if an individual is pregnant.

The conjugate source area preferably comprises dried conjugate. For example, the conjugate source area may be a conjugate pad on which conjugate has been dried. The conjugate pad is preferably in fluid communication with the membrane. In some embodiments the conjugate pad is moved into fluid communication with the membrane after the addition of sample to the sample application area. In another embodiment the conjugate source area is a portion of the membrane on which conjugate has been dried.

Dried conjugate is preferably resuspended and caused to flow by contacting the conjugate source area with wash buffer. In one embodiment the wash buffer comprises about 0.1% blocking agent, preferably a blocking protein such as casein. The wash buffer also preferably comprises about 0.1% detergent, preferably a non-ionic detergent such as Triton X100™. In one embodiment, the wash buffer comprises about 0.025% HEPES, about 0.85% sodium chloride, about 0.1% EDTA, about 1% mannitol, about 0.1% casein and about 1% Triton X100™ detergent.

In a further embodiment, the conjugate is suspended in buffer. The conjugate is caused to flow to the test area by the addition of the buffer comprising the conjugate to the conjugate source area.

In a particular embodiment the conjugate comprises protein A conjugated to colloidal gold. In other embodiments the conjugate comprises an antibody, preferably a monoclonal antibody, conjugated to colloidal gold. Preferably the colloidal gold has a particle size of about 20 to about 80 nanometers.

In another embodiment, the test strip additionally comprises a control area located on the membrane downstream of the test area. The control area preferably comprises a control binding agent that is able to bind the conjugate. For example, if the analyte of interest is an antibody and the conjugate comprises an antibody binding agent such as protein A, the control binding agent may be rabbit IgG. If the analyte of interest is an antigen and the conjugate comprises a monoclonal antibody that is specific for the antigen, the control binding agent may be, for example, protein A.

The test strip may comprise one or more additional components. A buffer pad may be in fluid communication with the conjugate source area, such that the addition of wash buffer to the buffer pad causes conjugate to flow from the conjugate source area and across the membrane to contact the test area. An absorbent strip and an absorbent pad may be located downstream of the membrane to absorb excess buffer as it passes across the membrane. A desiccant tablet may also be in proximity to the membrane to absorb excess liquid and moisture.

The test strip may optionally be present in a housing, such as a plastic housing. The housing preferably comprises a sample window located over the test and control areas, and a buffer window, located upstream of the test area.

A method of detecting an analyte in a liquid sample is also provided, comprising applying the sample to the test area of a membrane and subsequently contacting the test area with a conjugate that is able to bind the analyte of interest and provide a visual signal indicative of the binding.

BRIEF DESCRIPTION OF THE DRAWINGS

FIG. 2 shows a top view of a test card according to one aspect of the invention.

FIG. 3 shows a side view of a test card according to one aspect of the invention.

DETAILED DESCRIPTION OF THE PREFERRED EMBODIMENT

Figure 1:
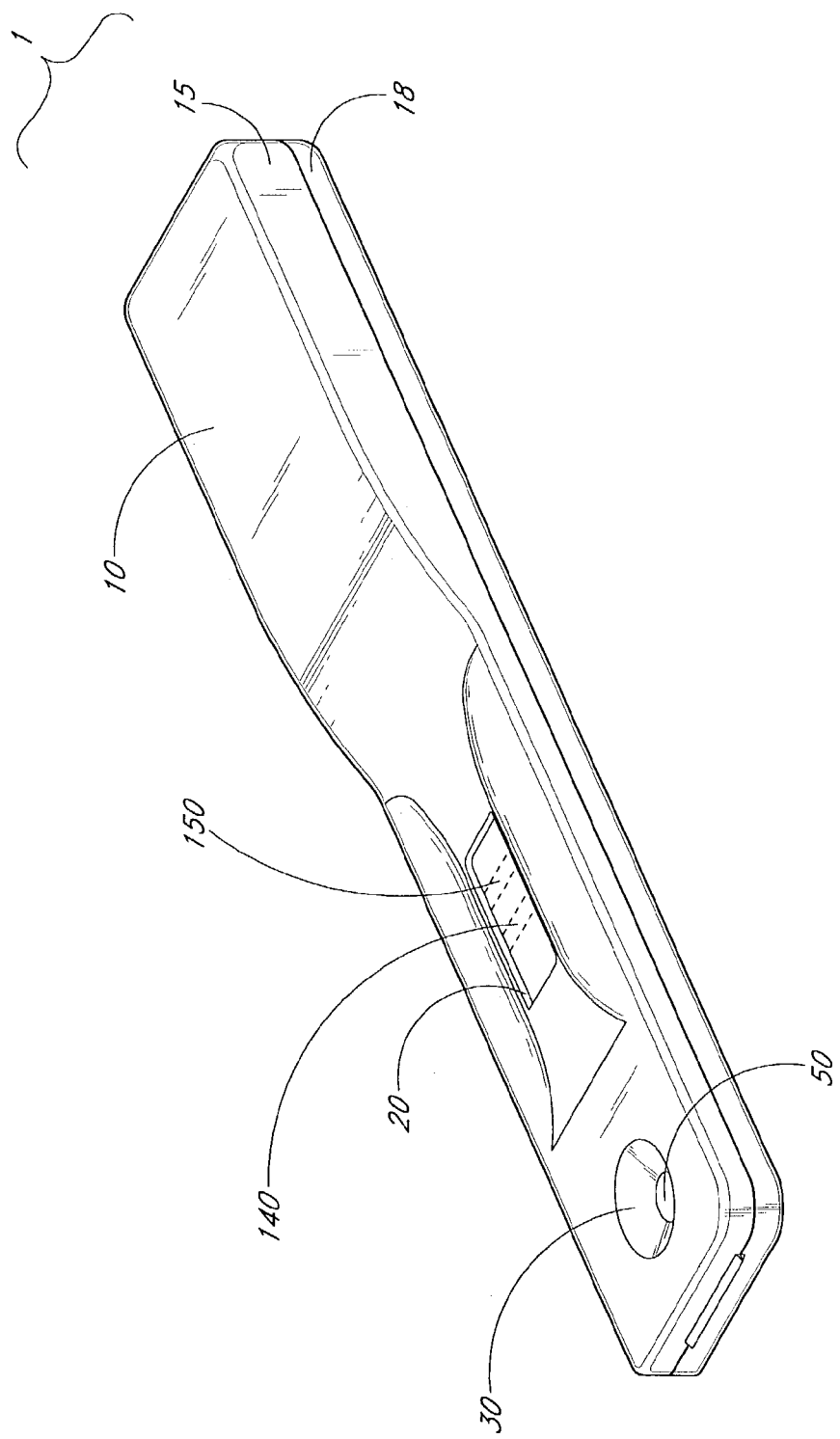
FIG. 1 shows a test card according to one aspect of the present invention.

Diagnostic devices and methods are provided for the rapid determination of the presence of an analyte in a sample. While generally described in terms of an immunodiagnostic device for the detection of an antibody or antigen in a sample, one of skill in the art will recognize that the present invention can readily be modified for the detection of any analyte of interest.

In the past, immunodiagnostic devices typically involved the premixing of a conjugate with the sample to be analyzed for the presence of an antibody. For example, in some devices dried conjugate was dissolved by addition of a liquid sample, allowing for premixing of the sample and the conjugate. The antibody to be detected, if present, bound to the conjugate and was visualized at a downstream test area comprising an immobilized antigen. However, in this system non-specific interaction of the conjugate with other antibodies or other compounds in the sample led to a quenching of the conjugate signal. As a result, a large amount of conjugate was necessary. Due to the large amount of conjugate used, the reaction took a long time to clear, extending the time needed for obtaining the results of the test. In addition, the sensitivity of the test was such that a significant amount of antigen was necessary at the test area in order to produce a visible positive signal.

The present invention overcomes the problems in the prior art by contacting the test area directly with the sample, allowing any analyte of interest to bind specifically to immobilized binding agent. For example, an antibody of interest can bind to immobilized antigen. Subsequently, conjugate is supplied to the test area with buffer. The solvent front of the buffer pushes out unbound compounds at the test area, reducing non-specific interactions with the conjugate. As a result, the required amount of conjugate is significantly reduced and the speed of the reaction is thereby increased. In addition, the sensitivity of the reaction is increased, allowing for the use of less antigen at the test area.

The described devices and methods may be used, for example, to diagnose a disease or disorder in a patient, such as human immunodeficiency virus (HIV) or hepatitis virus. They may also be used to determine if an individual is pregnant. Other uses will be apparent to those of skill in the art based on the disclosure below.

DEFINITIONS

Unless defined otherwise, all technical and scientific terms used herein have the same meaning as commonly understood by one of ordinary skill in the art to which this invention belongs. Any methods, devices and materials similar or equivalent to those described herein can be used in the practice of this invention.

An "analyte of interest" is any molecule or compound whose presence is to be identified in a sample. Analytes may include, without limitation, viral antigens, bacterial antigens, hormones, such as insulin, follicle stimulating hormone (FSH), thyrotropin, relaxin, somatotropin and gonadotropin, enzymes, immunoglobulins, cytokines, drugs, cancer antigens, antigenic polysaccharides, and nucleic acids. Other analytes that may be identified in samples using the provided methods and apparatus will be apparent to one of ordinary skill in the art. Particularly preferred analytes of interest include anti-HIV antibodies, anti-HCV antibodies and human chorionic gonadotropin (hCG).

The term "conjugate" refers to a composition that is configured to bind to an analyte of interest and produce a detectable signal. The conjugate typically comprises a binding component conjugated to a label. The binding component allows the conjugate to bind to the analyte of interest and optionally to a control compound. The label produces a detectable signal, preferably a visual signal. In one embodiment the visual signal is produced only upon binding of the conjugate to the analyte. In a preferred embodiment the analyte of interest is an antibody and the conjugate comprises a binding component that is able to bind antibodies. For example, the first binding component can be protein A, although other molecules that are able to bind antibodies can be used. In another embodiment the analyte of interest is an antigen and the binding component of the conjugate comprises an antibody that is able to bind the antigen. Preferably the antibody is a monoclonal antibody.

The label is any molecule or compound that can be attached or conjugated to the binding component and that can produce a detectable signal. A preferred label is colloidal gold. Alternatively, the label may be, for example, dyed latex particles, colloidal silver or other colloidal metals, colloidal black, or other components known in the art. Preferably, the label has a particle size such that it does not interfere with the ability of the binding component to bind the analyte of interest. For example, when the binding component is protein A, the label preferably has a particle size of from about 5 to about 120 nanometers, more preferably from about 20 to about 80 nanometers.

The conjugate is preferably prepared in a "conjugate buffer" that may stabilize and preserve the conjugate. In one embodiment, following preparation in conjugate buffer, the conjugate may be dried onto a "conjugate pad," as described in more detail below. Conjugate that is dried onto a substrate is considered to be "diffusably bound." The conjugate is "diffusably bound" if it is able to be caused to diffuse or flow, such as by contacting it with a buffer. For example, conjugate that has been diffusably bound to the conjugate source area by drying may be solubilized with buffer and thus caused to flow along the membrane of the test strip.

A "control conjugate" is a conjugate wherein the binding component is specific for a control compound. A control conjugate is preferably employed when it is likely that all of the conjugate will be bound to analyte on the test line and unavailable to serve as a control. The control compound is typically one that is known to be in the sample that is being analyzed and is capable of binding the control binding agent on the control stripe. Optionally the binding component of the control conjugate may be specific for a compound that is present in the control area of the test membrane.

The conjugate is preferably present in a "conjugate source area." The conjugate source area typically comprises conjugate that is diffusably bound thereto, such as dried conjugate. Alternatively, the conjugate source area may comprise conjugate that has been suspended in buffer, such as wash buffer or conjugate buffer. In one embodiment the conjugate source area is a conjugate pad, comprising dried conjugate, that is in fluid communication with the test membrane. In another embodiment the conjugate source area is a portion of the test membrane on which conjugate has been dried. In a further embodiment the conjugate source area is a buffer pad, to which buffer comprising conjugate may be added, that is in fluid communication with the test membrane. The conjugate source area is typically located upstream of the test area on the test membrane, such that upon addition of a solution comprising conjugate or solubilization of the diffusably bound conjugate, conjugate flows across the test membrane to contact the test area.

The conjugate is preferably solubilized with "wash buffer," as described in more detail below. Briefly, wash buffer is a buffered solution that preferably comprises a "blocking agent." Blocking agents are well known in the art and include any molecules or compounds that reduce non-specific interactions, such as non-specific antibody binding. Preferred blocking agents are proteins, such as casein and bovine serum albumin (BSA). Other blocking agents that may be used are commercially available and will be apparent to one of ordinary skill in the art.

"Sample buffer" is a buffered solution that preferably does not comprise conjugate. In some embodiments the sample buffer comprises a blocking agent, while in other embodiments it does not. Sample buffer may optionally be applied to the membrane prior to addition of the sample, as discussed in more detail below.

A "test membrane" is a solid support comprising a test area and, optionally, a control area. The sample to be analyzed is typically applied directly to the test membrane so that it contacts the test area and control area. The test membrane may be any solid support to which an analyte binding agent and a control binding agent can be attached. Preferably the test membrane is nitrocellulose.

The test membrane provides a lateral flow path for liquids. The test membrane and other components of the test strip are said to be in "fluid communication" if liquid, such as a liquid sample or buffer, can flow from one component to another. If components of the test strip are in contact with each other, they are in fluid communication. However, as will be recognized by one of skill in the art, direct contact between two particular components is not required for fluid communication.

"Test area," "test stripe" and "test line" are used interchangeably and refer to an area on the test membrane to which an analyte binding agent is attached.

An "analyte binding agent," "specific binding partner" or "binding component" is any molecule or compound that is configured to specifically bind to an analyte of interest. For example, and without limitation, the analyte binding agent may comprise antigens, antibodies, receptors, other polypeptides, peptides, haptens, lectins, nucleic acid, including oligonucleotides, or small molecules. In one embodiment the analyte binding agent is an antigen that is specific for an antibody that is to be detected in a sample. In another embodiment the analyte binding compound is an antibody that is specific for an antigen of interest.

"Control area," "control stripe" and "control line" are used interchangeably and refer to an area on the membrane to which a control binding agent is attached.

A "control binding agent" is any molecule or compound that is able to bind specifically to the conjugate or to a control conjugate.

"Test strip" refers to a complete apparatus that can be used to detect the presence of an analyte in a sample. The test strip preferably comprises at least a test membrane with a test area and a control area. As described below, the test strip may be present in a housing, such as a plastic housing. Alternatively, the test strip may be used without a housing. If present in a housing, the test strip and housing together may be referred to as a "test card."

"Test card window" and "sample window" refer to a hole in the plastic housing of a test card through which a sample may be applied. The test card window is preferably located above the test area and control area. The test card window also preferably allows for visualization of the test results.

"Buffer window" refers to a hole in the plastic housing of a test card through which buffer may be applied. In one embodiment the buffer window is preferably located to allow buffer to be applied to a buffer pad. In another embodiment the buffer window is located to allow application of buffer directly to the test membrane.

"Volume indicator window" refers to a hole in the plastic housing of a test card through which a visible sample volume indicator can be seen. The volume indicator window is located downstream of the sample window. The sample volume indicator signals that an acceptable sample volume has contacted the test area. A sample volume indicator may be, for example, methylene blue or other colored compound that has been applied to the membrane just upstream of the volume indicator window. The sample volume indicator is carried across the volume indicator window by the movement of the sample, producing a visual signal in the window. In other embodiments the sample volume indicator is a compound that changes color when contacted by the sample, such as a pH indicator. Typically, a sample volume indicator is used when a large sample volume is necessary, such as when an analyte of interest is believed to be present at a low concentration in a sample. For example, a sample volume indicator is preferably used when urine is being analyzed for the presence of hCG.

"Sample" refers to any material that is to be analyzed for the presence of an analyte of interest. The sample is preferably in liquid form. Exemplary samples include, without limitation, bodily fluids such as whole blood, plasma, serum, saliva and urine. As described in more detail below, the sample may be a solid. However, in this case the sample is preferably solubilized or extracted prior to use in the test.

The "sample application area" is the location on the membrane to which sample is applied. The sample application area is preferably located downstream of the conjugate source area and upstream of the test area. More preferably, the sample application area comprises the test area. Sample may be applied to the sample application area directly, such as by pipette, or indirectly, such as through a wick that is in contact with the membrane.

The term "antibody" is used in its broadest sense and includes, for example and without limitation, whole antibodies as well as single chain antibodies, antibody fragments, and chimeric antibodies, so long as they retain the desired binding specificity.

The Test Card

The diagnostic devices disclosed herein preferably comprise a test card 1, as illustrated in FIGS. 1-3. FIG. 1 illustrates a test card 1 comprising a plastic housing 10, with an upper portion 15 and a lower portion 18 that snap together. There are two openings within the upper portion 15 of the plastic housing 10: a sample window 20 and a buffer window 30. The sample window 20 allows for the application of a sample to the sample application area of a membrane contained within the plastic housing 10. The sample application area preferably comprises a test area 140. A control area 150 is preferably located downstream of the test area 140 on the membrane. The buffer window 30, allows for the application of buffer to the conjugate source area 50. The membrane is part of a test strip that is described in detail below.

A further optional volume indicator window (not shown) is located downstream of the test area in some embodiments. The volume indicator window, if present, allows the user to visualize an indicator, such as a color change, on the membrane downstream of the test area. The indicator signals that a sufficient volume of sample has contacted the test area and that the user can proceed to contact the test area with conjugate to detect bound analyte as described below, such as by applying buffer to the conjugate source area.

FIG. 2 illustrates a top view of the test card 1, showing the sample window 20 and the buffer window 30 within the plastic housing 10. The test area of the membrane 140 is accessible through the sample window 20 and the conjugate source area 50 is accessible through the buffer window 30. A control area 150 is located downstream of the test area 140. Although illustrated with a sample window 40 that is rectangular and a buffer window 30 that is circular, the windows can be of any shape or size. However, they are preferably shaped and sized to direct the sample to the sample application area of the membrane 40 and the buffer to the conjugate source area 50. In addition, the sample window is configured to allow for the visualization of the test area 140, if a positive test result is obtained, and the control area 150.

FIG. 3 illustrates a side view of an exemplary test card 1. The upper portion 15 and lower portion 18 of the plastic housing 10 are shown. The enlarged end (60) of the upper portion 15 of the plastic housing 10 that is distal to the buffer window (not shown) allows for the placement of absorbent material, such as an absorbent pad or desiccant tablet within the test card (1). The size of the enlarged end (60) will vary depending on the amount of absorbent material used, which in turn will depend on the volume of sample and buffer employed in the test.

The Test Strip

A test strip comprises a test membrane with at least one test area. An analyte binding agent that is specific for an analyte of interest is bound or otherwise immobilized at the test area. At least a portion of the test area becomes visible upon completion of the test if the analyte of interest is present in the sample. In a particular embodiment the test area comprises immobilized antigen and the test allows for the identification of particular antibodies in a sample such as a biological fluid. In another embodiment the test area comprises bound antibody and the test allows for the identification of a particular antigen in a sample.

The sample is applied to a sample application area that is located downstream from the conjugate source area, for example downstream of the conjugate pad. In the preferred embodiment the sample application area comprises the test area. However, in other embodiments the sample application area is located upstream of the test area and sample flows from the sample application area to the test area.

Figure 4:
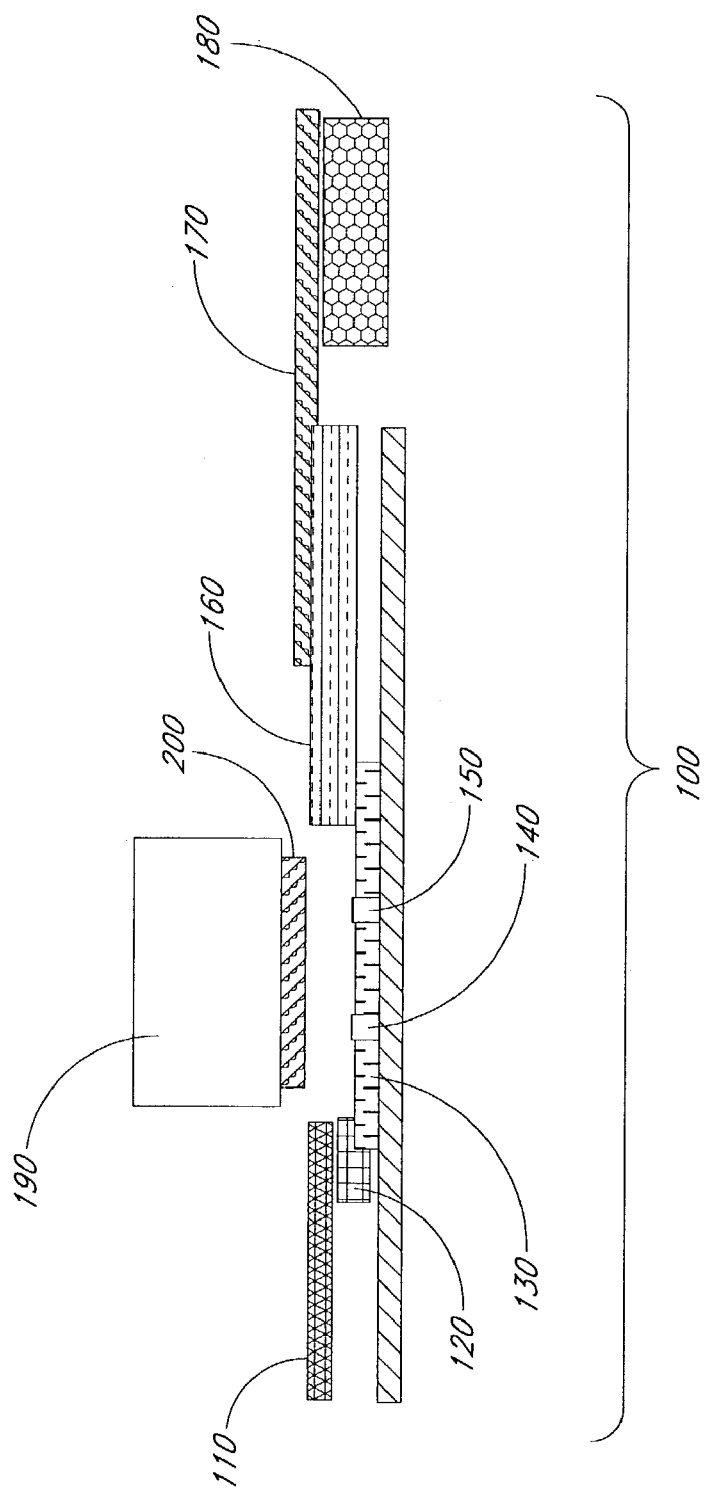
FIG. 4 shows a cut away view of the components that comprise a test strip according to one embodiment.

A preferred embodiment of the test strip is diagrammed in FIG. 4. A test strip 100 for testing a sample for the presence of an analyte of interest, such as an antibody, preferably comprises a buffer pad 110 in contact with a conjugate pad 120. The conjugate pad 120 is in turn in contact with a test membrane 130 comprising a test area 140 and a control area 150. The membrane 130 is in turn in contact with an absorbent pad 160. The absorbent pad 160 is optionally in contact with a further absorbent paper 170. The absorbent pad 160 and/or the optional absorbent paper 170 may be in further contact with an optional desiccant 180, such as a desiccant tablet.

In some embodiments a removable filter holder 190 is attached to the test strip 100. The filter holder 190 comprises a filter paper 200. When the filter holder 190 is attached to the test strip 100, the filter paper 200 is located directly above the sample application area, which preferably comprises the test area 140 and control area 150.

Figure 7:
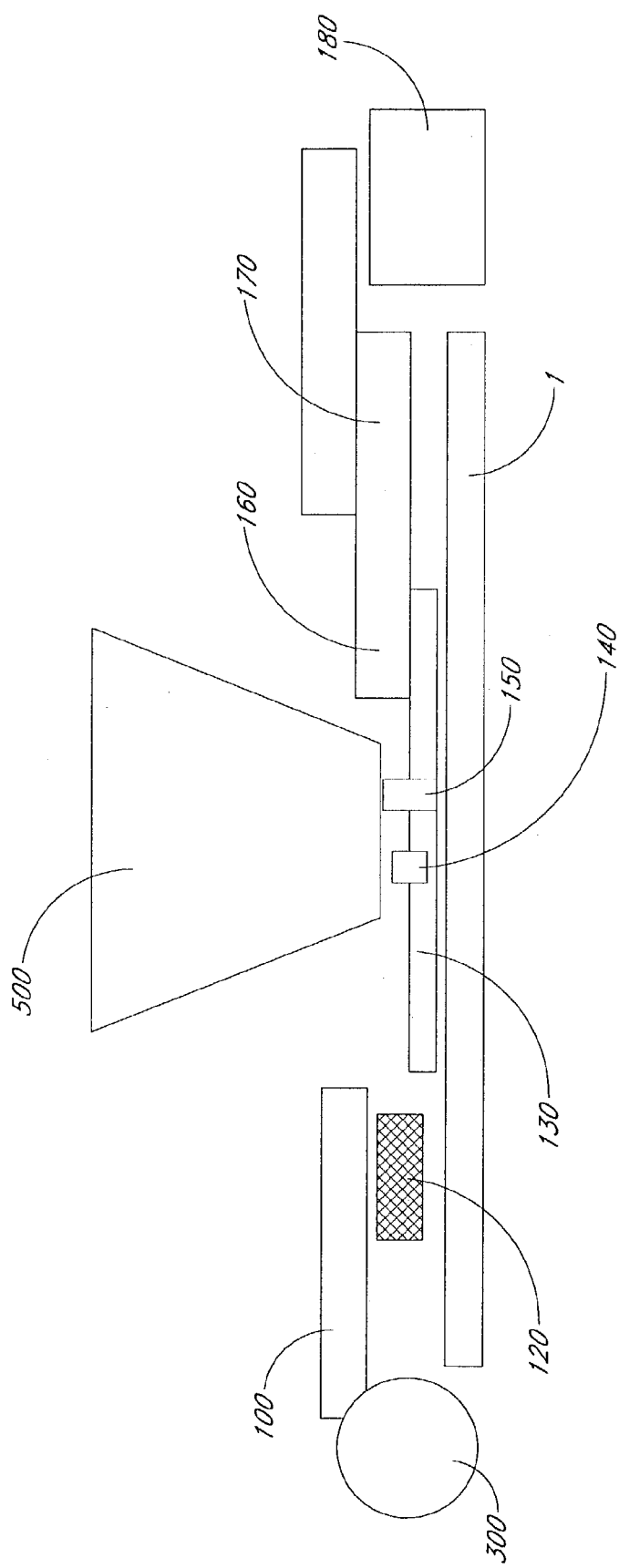
FIG. 7 shows a test strip with a sample cup according to a further aspect of the invention.

Sufficient sample must be provided to the test area to ensure a visible positive reading upon completion of the test if the analyte is present in the sample. Thus, for analytes that are suspected to be at a low concentration in the sample, for example antigens such as hCG in urine, a greater sample volume is required. The test strip 100 may be configured to accept the larger sample volumes. One such embodiment is illustrated in FIG. 7, where a sample cup 500 is attached to the test strip 100. The sample cup 500 comprises a container for holding a volume of a liquid sample. Typically the sample cup will have an opening in the bottom that allows the sample to flow out of the sample cup 500 and contact the test membrane 130. Thus, the sample cup 500 is located so that sample flows from the sample cup 500 to the sample application area of the test membrane 130 and contacts the test area 140 and control area 150. Preferably the sample application area comprises the test area 140 and control area 150 and the sample cup 500 is located directly over the test area 140 and control area 150. The sample cup 500 may optionally comprise a filter through which the sample passes prior to contacting the test membrane.

The sample may be deposited in the sample cup while it is attached to the test card. In another embodiment the sample is placed in the test cup and the test cup is subsequently attached to the test card and the sample allowed to flow to the sample application area.

It is desirable to ensure that a volume of sample comprising a detectable amount of analyte, if present, has contacted the test area 140 prior to causing the conjugate to flow to the test area 140. A sample volume indicator, such as an indicator dye, located downstream of the test area 140 and control area 150 may be used to determine that a sufficient quantity of sample has contacted the test area 140 and control area 150. For example, an indicator dye such as methylene blue may be applied to the absorbent pad 160 or the absorbent paper 170 downstream of the test membrane. The flow of the liquid sample along the absorbent pad 160 or the absorbent paper 170 causes the dye to flow, creating a visual signal, for example, a visible blue color. The signal may be observed through a volume indicator window in a window in the test card (not shown).

In some embodiments, particularly those in which a large sample volume (greater than about 50 μl) are to be applied, the conjugate pad 120 is not in fluid communication with the test membrane 130. One such embodiment is illustrated in FIG. 7. The separation of the conjugate pad 120 and test membrane 130 prevents mixing of the conjugate and sample prior to the sample contacting the test area 140. After the sample has contacted the test area 140 and control area 150, the conjugate pad 120 is moved to be in fluid communication with the test membrane 130. Buffer is then applied to the buffer pad 110 to start the test. Buffer may be applied to the buffer pad 110 directly through a buffer window, or by breaking an ampoule 300 holding the buffer, thus causing the buffer to flow to the buffer pad 110. In one embodiment buffer is applied to the buffer pad 110 prior to moving the conjugate pad 120 to be in fluid communication with the membrane 130. In alternative embodiments buffer is applied directly to the conjugate pad 120.

The method by which the conjugate pad 120 is caused to move into fluid communication with the membrane 130 is not limited in any way. In one embodiment the user slides a movable portion of the housing to which the conjugate pad 120 and optionally the buffer pad 110 are attached, thus bringing the conjugate pad 120 into contact with the membrane 130. The mechanism for moving the conjugate pad 120 into fluid communication with the test membrane 110 preferably also causes the buffer ampoule 300 to break. The mechanism may also cause the sample cup 500 to be removed from the test strip 110.

A desiccant tablet 180 is preferably in fluid communication with the absorbent paper 170. The size of the desiccant tablet 180 is chosen to be able to absorb the total volume of sample applied to the test membrane 130. The desiccant tablet and any other absorbent material is located downstream of the sample application area and facilitates the flow of sample across the test area.

In other embodiments the sample cup is replaced with a wick that is contacted with a liquid sample. The sample flows along the wick to the sample application area of the test membrane and contacts the test area and control area. In a particular embodiment the wick is placed in the urine stream to analyze urine for the presence of an analyte, such as hCG. In these embodiments the conjugate pad is preferably not in fluid communication with the test membrane during the time that sample is being applied to the wick. After sufficient sample has contacted the test area, the conjugate pad is moved to contact the test membrane. The mechanism for moving the conjugate pad may also serve to remove the wick. Buffer is subsequently added to the buffer pad or directly to the conjugate pad to begin the test. The buffer may be added directly to the buffer pad through a buffer window, as described above. Alternatively, the buffer may be present in an ampoule within the test card and caused to flow to the buffer pad and/or conjugate pad by breaking or otherwise opening the ampoule.

The test strip is preferably contained within a housing, as shown in FIG. 2 and described above.

Figure 5:
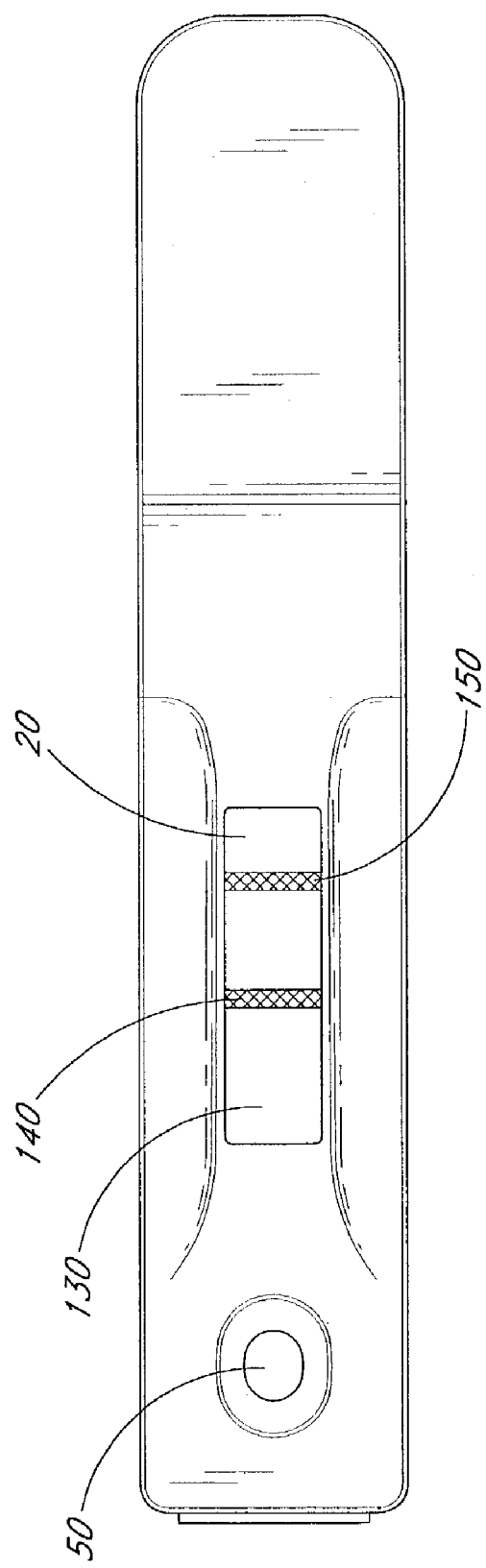
FIG. 5 shows a test card with a positive result indicating that the analyte of interest was detected in the sample.
Figure 6:
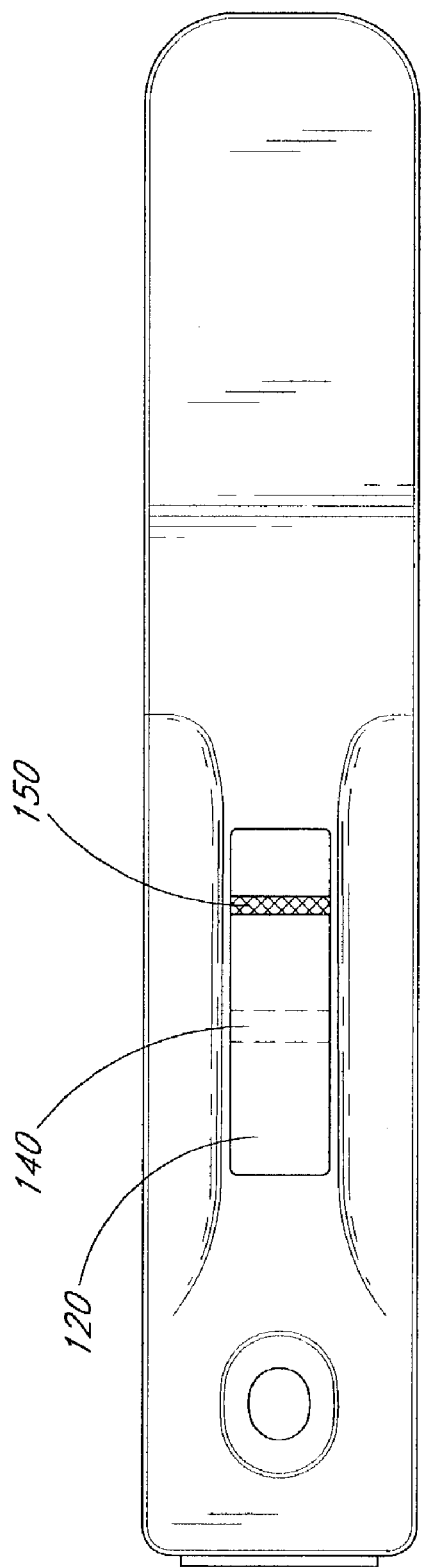
FIG. 6 shows a test card with a negative result, indicating that the analyte of interest was not detected in the sample.

FIG. 5 illustrates a positive test result, indicating the presence of the analyte of interest in a sample. The test area 140 of the membrane 130 is visible as a line across the sample window 20. In addition, the control area 150 is visible as a line across the sample window 20, indicating that the conjugate flowed from the conjugate source area 50 across the test area 140. In contrast, a negative result is illustrated in FIG. 6. With a negative result, only the control area 150 is visible as a line across the sample window 20. Again, the control indicates that the conjugate flowed from conjugate source area 50 across the test area 140. Thus, the lack of a line at the test area 140 is a result of the lack of bound analyte of interest.

Use of the Test Strip

A sample to be tested for the presence of a particular analyte of interest is applied to the sample application area of the test membrane such that it contacts the test area. In the preferred embodiment, the sample is applied to the membrane and allowed to contact the test area prior to the conjugate contacting the test area. Thus, analyte of interest in the sample, if present, has the opportunity to bind to the analyte binding agent in the test area prior to conjugate binding.

If the test strip is in a housing, the sample is preferably applied through a sample window. In this case, the membrane comprises a sample application area that is accessible through the sample window. Preferably the sample application area comprises at least one positive test area. More preferably the sample application area comprises a test area and a control area. Alternatively the sample may be applied through a wick or cup, such that it flows to the sample application area of the membrane and contacts the test and control areas.

If the test strip is not in a housing, the sample may be applied directly to the sample application area of the membrane, preferably comprising the test area and the control area. Alternatively, the sample may be applied to the membrane at a sample application area upstream from the test area and allowed to flow across the membrane to contact the test area. Preferably, however, the sample is allowed to contact the test area prior to addition of conjugate to the membrane.

In one embodiment the sample is collected or placed in a sample cup. The cup is attached to the housing and allows the sample to flow to the sample application area of the membrane and contact the test area and control area. A sample cup is preferably used if a sample volume greater than about 10 μl, is to be used. The sample cup may optionally comprise a filter through which the sample passes prior to contacting the membrane.

In a further embodiment, the sample is applied to a wick that is in contact with the membrane. The wick allows the sample to travel to the sample application area of the membrane and contact the test and control areas. The wick is preferably comprised of glass paper, polyester, cellulose, or another material that will allow the sample to migrate to the membrane comprising the test area. If the test card is in a housing, the wick may protrude from the housing, allowing access to the wick for application of the sample. For example, if the presence of a particular analyte is to be determined in urine, such as hCG, the wick may be placed in the urine stream of the subject being tested. In another embodiment the wick may be brought into contact with the sample to be analyzed, for example bodily fluids such as saliva.

The sample to be tested is preferably applied to the sample application area of the membrane in liquid form. Exemplary samples that can be analyzed include, without limitation, serum, plasma, whole blood, saliva and urine. Solid or semi-solid samples may be solubilized and applied to the membrane or extracted prior to application.

In other embodiments, sample buffer that preferably does not contain conjugate is applied to the membrane prior to application of the sample. In some embodiments the sample buffer comprises a blocking agent. Preferably the sample buffer is applied to the membrane at the sample application area. From about 1 to about 25 μl of sample buffer is preferably applied to the membrane, more preferably from about 1 to about 10 μl, yet more preferably about 1 to 5 μl. In a particular embodiment 5 μl of sample buffer is applied to the sample application area of the membrane, followed by 5 μl of serum, plasma, whole blood or other liquid sample. The addition of sample buffer prior to application of the wash buffer is particularly preferred in testing for HCV, as described below, and when viscous samples are used. The use of sample buffer increases the sensitivity of the test and causes viscous samples to flow faster.

Sample buffer preferably comprises a buffering agent and a preservative. Optionally, it may also comprise one or more detergents and/or sugars. Any buffering agent may be used, preferably in an amount that maintains the desired pH of the sample buffer. Preferably the pH of the sample buffer is from about 7.2 to about 7.6. For example, and without limitation, the buffer may be selected from the group consisting of HEPES, Tris and phosphate buffers. In a preferred embodiment the sample buffer comprises from about 0.01% to about 0.5% HEPES, more preferably from about 0.02 to about 0.05% HEPES. In another embodiment the sample buffer comprises from about 0.01% to about 0.5% phosphate, more preferably from about 0.02 to about 0.05% phosphate. One of skill in the art will be able to adjust the amount of buffering agent to maintain the desired pH.

The sample buffer also preferably comprises a preservative, such as sodium azide or Proclin. In a preferred embodiment the sample buffer comprises from about 0.1% to about 1.0% sodium azide, more preferably from about 0.1% to about 0.2%, yet more preferably about 0.2%.

Depending on the nature of the sample to be tested, the sample is optionally applied to the membrane through a filter. Exemplary sample materials that are preferably filtered include whole blood, fecal samples, urine, food extracts and dirt extracts. In one embodiment whole blood is applied through a membrane filter. The filter removes contaminants and allows analytes, such as antibodies to pass through, thus increasing the sensitivity of the test. The filter is preferably encased in a holder that can be attached to the test card or test strip as necessary. If attached to a test card, the filter is preferably attached directly above the sample window. Filter media will be chosen based on the type of sample to be filtered. Such selection is within the ability of the skilled artisan. For example, for whole blood samples the filter material may be, without limitation, Pall BTS-SP300™.

As discussed above, the filter is preferably attached to the test strip by a removable filter holder, although for particular applications the filter could be permanently affixed. The filter holder is typically a device that snaps onto the housing of the test card. The design and type of the device can vary, but it is typically formed from polystyrene, polyethylene, polypropylene or other plastic.

The test area is a portion of the membrane that is coated with a binding agent, preferably a protein, that is capable of specific binding to the analyte of interest. For example, the positive test area may be coated with antigen that is specific for an antibody of interest. In particular embodiments, the test area comprises bound HIV antigen or hepatitis antigen, as described in more detail in the Examples below. When the test area comprises antigen, preferably from about 0.025 to about 0.4 µg of antigen are used.

In other embodiments an antibody that is specific for an antigen of interest is immobilized at the test area. The antibody may be a polyclonal or monoclonal antibody. When the test area comprises antibody, preferably from about 0.1 to about 20 µg of antibody are applied, more preferably from about 0.2 to about 2 µg, even more preferably from about 0.5 to about 1 µg. In a particular embodiment the test area comprises an antibody to hCG, preferably a monoclonal antibody to hCG.

The binding agent may be applied to the membrane in any desired pattern; thus the visible result of a positive test may be any shape. In a preferred embodiment the test area is linear, forming a line stretching from one side of the membrane to the other, such that a vertical line appears across the sample window if a positive result is obtained, indicating the presence of the analyte in the sample. In other embodiments, the test area is shaped like a symbol, such as a "+."

It is possible to test for more than one type of analyte in a single test strip. In this case, additional positive test areas are prepared on the test membrane. For example, a second positive test area may comprise antigen to a second type of antibody or an antibody to a second type of antigen. The binding agent at an additional positive test area is not necessarily of the same type as the binding agent at a first test area. Thus, the binding agent at a first test area may be an antibody, while a binding agent at a second test area may be an antigen. In this way a sample may be analyzed for the presence of more than one type of analyte.

Each additional positive test area may be a different shape from the first test area, to allow the user to easily distinguish the nature of the positive result. Depending on the type of the additional analytes to be tested for, additional conjugates that bind the various analytes may be necessary. For example, if the analytes of interest are two different antibodies, a single conjugate comprising protein A may be used. However, if one analyte is an antibody and a second analyte is an antigen, two different conjugates would be required, one that specifically binds the antibody and one that specifically binds the antigen.

The control area preferably comprises a control binding agent that will bind to the conjugate. By locating the control area downstream from the positive test area, a reaction at the control area will indicate that the conjugate migrated past the test area, where it was available to react if the analyte of interest was present. If the conjugate is designed to recognize an antibody, the control area preferably comprises an immunoglobulin, such as rabbit IgG. If the conjugate comprises an antibody, the control area preferably comprises an antibody binding agent such as protein A. The control area may be any desired shape, such as a line or a symbol, for example "-."

In other embodiments the control area comprises a control binding agent that binds to a control conjugate. For example, the control area may comprise β-gal and the control conjugate may comprise β-galactosidase conjugated to gold.

The binding agent and control binding agent may be applied to the test membrane by any method known in the art. They are typically applied by contacting the test membrane with the binding agent, such as by spraying or contacting on the test membrane using a pump dispensing system. Such systems are available commercially, for example from Kinematic Automation.

When the sample contacts the test area, if the analyte of interest is present in the sample it will bind to the binding agent on the test area. Excess unbound analyte is washed away from the test area by the migration of buffer along the membrane as described below.

After the sample is applied to the membrane, wash buffer is applied to test membrane. Preferably from about 1 to about 20, more preferably from about 1 to 5 drops of wash buffer are initially applied. Additional wash buffer can subsequently be applied if necessary to clear the reaction.

The wash buffer preferably carries the conjugate to the test area. Wash buffer may be applied directly to the test membrane. In the preferred embodiment, however, wash buffer is applied to an upstream buffer pad from which it flows to the test membrane. The buffer pad may be made of any material that can contain the buffer and allow it to flow through to the membrane at a desired rate. For example, the buffer pad may be comprised of one or more materials selected from the group consisting of glass paper, cellulose and polyester. In a preferred embodiment the buffer pad is Whatman GF/DVA glass paper. The skilled artisan will be able to select an appropriate material for the buffer pad based on such factors as the housing design of the lateral flow test strip, the desired flow rate, and the amount of buffer that is to be held by the buffer pad.

The wash buffer may be applied directly to the buffer pad, such as with a pipette or dropper. However, in another embodiment the appropriate amount of wash buffer is present in a container that is adjacent to the buffer pad. For example, the wash buffer may be contained in a glass or plastic ampoule. Following addition of the test sample, the container comprising the was buffer is broken or otherwise opened, allowing the wash buffer to contact the buffer pad.

The composition of the wash buffer may be varied to increase the sensitivity of the test. Preferably, the wash buffer comprises a buffering agent, a preservative, a detergent, sugar and other materials that act to reduce background and/or non-specific binding.

Any buffering agent may be used that maintains the desired pH of the buffer, preferably about 7.2 to about 7.6. For example, and without limitation, the buffer may be selected from the group consisting of HEPES, Tris and phosphate buffer. In a preferred embodiment the wash buffer comprises from about 0.01% to about 0.5% HEPES, more preferably from about 0.02 to about 0.2% HEPES and even more preferably from about 0.02 to about 0.05% HEPES. In a particularly preferred embodiment the wash buffer comprises 0.025% HEPES.

The wash buffer may also comprise a preservative such as sodium azide or Proclin. In a preferred embodiment the wash buffer comprises about 0.1 to about 0.5% sodium azide, more preferably about 0.1 to about 0.2%.

Sodium chloride or a comparable salt is preferably present at a concentration of about 1%, more preferably about 0.85%. EDTA may be present, preferably at a concentration of about 0.1%. A sugar, such as mannitol, may also be present. Preferred mannitol concentrations are from about 1% to about 5%. In a preferred embodiment the mannitol concentration is about 1%.

A blocking agent is preferably present in the wash buffer as well. The blocking agent may be any blocking agent known in the art. Preferably the blocking agent is a protein, such as casein or bovine serum albumin (BSA). The blocking agent is preferably present in the wash buffer at a concentration from about 0.01 to about 0.51%, more preferably from about 0.02 to about 0.2%. In a particularly preferred embodiment casein is present in the wash buffer at a concentration of about 0.1%.

The wash buffer typically also comprises a detergent, preferably a non-ionic detergent such as Triton X100™ or Tween. Preferably, the detergent is present at a concentration of about 0.05 to about 1%, more preferably about 0.1 to about 0.5%. In a particularly preferred embodiment the was buffer comprises Triton X100 at a concentration of about 0.1%.

The pH of the wash buffer is adjusted to between about 7 and 8, more preferably to between about 7.2 and 7.6. In a particularly preferred embodiment the pH of the wash buffer is about 7.2.

The test strip also comprises a conjugate source area. In a preferred embodiment the test strip comprises a conjugate pad on which conjugate has been dried, as described below. Wash buffer flows from the buffer pad to the conjugate pad, with which it is in contact. The conjugate pad is, in turn, in contact with the test membrane. In some embodiments, however, the conjugate pad is brought into contact with the membrane after addition of the sample. In particular, when a large sample volume is used, the conjugate pad is preferably brought into contact with the membrane after the sample has contacted the test area.

Sufficient wash buffer is applied to the buffer pad to dissolve the conjugate diffusably bound to the conjugate pad and cause the conjugate to flow along the test membrane to the test line and control line. The amount of buffer to be used can be determined by one of ordinary skill in the art based on such factors as the amount of conjugate bound on the conjugate pad, the size of the membrane and the amount of sample to be analyzed. Preferably, from 1 to 10 drops of buffer solution are applied to the buffer pad when the buffer pad is approximately 2 cm by 5 mm, more preferably from 2 to five drops and even more preferably 3 to 4 drops.

In alternative embodiments a conjugate pad is not present. In one alternative embodiment the conjugate is present in the wash buffer at a concentration ranging from about 0.2 OD to about 1.0 OD/ml. The wash buffer containing the conjugate may be applied to the buffer pad. The conjugate thus flows with the wash buffer from the buffer pad to the membrane where it contacts the test area and control area. In another embodiment, wash buffer containing conjugate is applied directly to the test membrane. The wash buffer containing the conjugate may be present in an ampoule, and caused to flow to the membrane by breaking or otherwise opening the ampoule. The wash buffer containing the conjugate is preferably applied to the membrane at a point upstream of the test area. However, in some embodiments the wash buffer comprising conjugate is applied directly to the test area after the sample has been applied.

In another embodiment the conjugate is diffusably bound, such as by drying, directly on the membrane that comprises the test area and control area. Wash buffer may then be applied to a buffer pad that is in contact with the membrane, or directly to the test membrane. The wash buffer dissolves the dried conjugate and carries it along the test membrane to the test area and control area.

The wash buffer comprising conjugate preferably contacts the test area after the sample has been applied and any analyte present in the sample has had the opportunity to bind the immobilized binding agent. Thus, the wash buffer is preferably applied to the test strip after the application of the sample to the test area.

The conjugate, described in detail above, is prepared for use in the test by dilution in conjugate buffer. Preferably working conjugate is prepared by diluting conjugate in conjugate buffer to approximately 3 OD/mL. The composition of the conjugate buffer may be varied depending on the nature of the conjugate. Exemplary conjugate buffer comprises a buffer such as HEPES, Tris, phosphate or other similar buffer known in the art. A preferred conjugate buffer comprises about 0.02 to 0.2% HEPES buffer, more preferably about 0.025% HEPES. The conjugate buffer may also comprise a salt, preferably sodium chloride. Sodium chloride is added to a concentration of about 0.1%, more preferably about 0.85%. A preservative may also be included in the conjugate buffer, such as sodium azide or Proclin, at a concentration of about 0.1 to about 0.2%.

The conjugate buffer also preferably comprises EDTA (about 0.1%), casein at a concentration of about 0.02 to about 0.2%, more preferably about 0.15%, bovine serum albumin (BSA) at a concentration of about 0.5 to about 3%, more preferably about 1%, mannitol at a concentration of about 1% to about 5%, more preferably about 1%, sucrose at a concentration of about 1% to about 5%, more preferably about 1%. Triton X100 may be included in the buffer, preferably at a concentration of about 0.1 to about 0.5%, more preferably about 0.1%.

The conjugate buffer is preferably adjusted to a pH of about 7.2 to about 7.6, more preferably to a pH of about 7.2.

In one embodiment, following preparation of the working conjugate by dilution of the conjugate in the conjugate buffer, the working conjugate is dried onto a conjugate pad, such as by vacuum drying. The conjugate pad is preferably cut into the appropriate size strips for use in the test strip. In the examples below, the conjugate pad is cut into 5 mm×5 mm strips.

The conjugate pad is preferably comprised of glass fiber, glass paper, polyester or cellulose paper. Such materials are well known in the art and are available, for example, from Millipore, S&S and Whatman. In a preferred embodiment the conjugate pad is a commercially available glass fiber conjugate pad GFCP203000 (Millipore).

As described above, the wash buffer dissolves the dried conjugate and causes it to flow from the conjugate pad and along the test membrane past the test area and control area.

The test membrane can be any material to which a protein or other binding agent can be attached, either covalently or non-covalently, and along which the conjugate can flow with the wash buffer. The test membrane is preferably a nitrocellulose membrane. Other membranes with higher or lower flow rates can be selected for use as the test membrane by one of skill in the art based on such factors as the desired sensitivity and test times and cost.

As the conjugate flows with the wash buffer across the membrane, it contacts the test area. If the analyte of interest is present and bound to the binding agent on the test area, conjugate in the buffer will bind to the analyte.

The wash buffer comprising conjugate that did not bind at the test area will continue to flow across the membrane to the control area. Conjugate will bind to the control binding agent. The wash buffer will also carry unbound sample from the test and control areas.

Wash buffer including unbound conjugate and unbound sample will then flow to an absorbent pad that is in contact with the downstream end of the membrane. The absorbent pad can be made of any absorbent material known in the art. Preferably, the absorbent pad is an absorbent paper, such as S&S 900™ paper. Other absorbent papers are well known in the art and may be chosen by the skilled artisan depending on the final configuration of the test strip.

The wash buffer may continue to flow through the absorbent pad and into an absorbent paper that is in contact with the absorbent pad. The absorbent paper is preferably used if a large amount of buffer must be absorbed.

A molecular sieve desiccant tablet may also be incorporated into the test strip. In one embodiment the buffer with unbound conjugate flows from the absorbent paper into the desiccant tablet with which the paper is in contact. The desiccant tablet holds the absorbed fluid and prevents backflow into the test strip.

The desiccant tablet may also keep the test strip dry prior to use. A preferred desiccant tablet is a 0.395 g. Tri-Sorb tablet, available from Sud-Chemie (product number 43-01).

The skilled artisan can select the appropriate size and material for the absorbent pad, absorbent paper and desiccant tablet depending on the final configuration of the test strip, including the total volume of sample and buffer that is to be used.

The entire test strip is preferably contained within a housing, such as a plastic housing. As described above, in one embodiment the housing comprises a sample window through which the sample can be added to the membrane containing the test and control areas. The housing may also comprise a buffer window through which buffer can be applied to the buffer pad or to the membrane. The housing may also comprise a volume indicator window, through which a signal can be viewed indicating that a sufficient sample volume has contacted the test area. A sufficient sample volume is a volume of sample that is estimated to contain enough analyte of interest, if present, that a visible signal will be produced at the test are upon completion of the test if the analyte is present in the sample. For example, for a test to detect hCG in urine, a sufficient sample volume is about 200 µl of urine.

The results of the test are preferably read from about 1 to about 5 minutes after addition of wash buffer to the test strip. In one embodiment results are read from about 2 to 4 minutes after addition of wash buffer, more preferably from about 3 to 4 minutes after addition of wash buffer. In a particularly preferred embodiment results are read 1 minute after addition of wash buffer. As shown in FIG. 7, for a positive result, the test line (300) will become visible. A visible control stripe (400) indicates that the test functioned correctly. As illustrated in FIG. 6, if the control line (400) is visible but the test line is not, a negative result is indicated.

EXAMPLE 1

Construction of an HIV Test Card

A lateral flow rapid visual test for the detection of antibodies to human immunodeficiency virus was prepared. The arrangement of the test strips was essentially as illustrated in FIG. 1.

The test strips comprised a plastic backing (6 cm×5 mm) with adhesive on both sides. The plastic backing was between about 2 mil and about 20 mil in thickness.

A test line and a control line were prepared on nitrocellulose membrane (Millipore HF09004) by spraying with a pump dispensing system (Kinematic Automation). The test line comprised a vertical line of HIV antigen. The HIV antigen was a mixture of HIV-1 recombinant glycoprotein antigens (GP120 (about 0.15 mg/ml) and P24 (about 0.1 mg/ml)) and HIV-2 recombinant glyco-protein antigen (GP36 (about 0.5 mg/ml), at a concentration of about 0.5 to about 1.0 mg/ml prepared in PBS comprising 5% trehalose. A total amount of from about 0.1 to about 0.5 µg of antigen was applied to the test area in a vertical line.

Other test strips were prepared comprising a single HIV-1 or HIV-2 antigen on the test line.

For all test strips the control area comprised a vertical line of control antibody. The control antibody was rabbit IgG diluted to 1 mg/mL in PBS comprising 5% Trehalose. A total amount of control antigen sufficient to produce a visible control line upon conjugate binding was applied to the control area.

For each test strip, the appropriate nitrocellulose membrane was cut to a size of about 2.5 cm×5 mm and attached to the plastic backing.

Protein A attached to colloidal gold, commercially available from Sigma, was used as the conjugate for the test. The conjugate was diluted in conjugate buffer to a concentration of approximately 3 OD/ml. The conjugate buffer comprised 0.25% HEPES, 0.85% sodium chloride, 0.1% sodium azide, 0.1% EDTA, 0.1% casein, 1% bovine serum albumin, 1% mannitol, 5% sucrose, and 0.1% Triton X100. The buffer was adjusted to a pH of 7.2.

Conjugate was applied to a glass fiber conjugate pad (Millipore GFCP203000), which was dried and cut into 5 mm×5 mm strips. A strip was attached to the end of the nitrocellulose membrane closest to the test area of each test strip.

A Whatman GF/DVA glass paper buffer pad (2 cm×5 mm) was then attached to the dried conjugate pad of each test strip to serve as the buffer pad.

An absorbent pad (2 cm×5 mm) made of S&S 900 paper was attached to the end of the nitrocellulose membrane closest to the control area and a further absorbent paper (2.5 cm×5 mm; S&S 470) was attached to the absorbent pad. The absorbent paper was in turn in contact with a 0.395 g desiccant tablet (Tri-Sorb, Sud-Chemie).

The test strip was placed in a plastic housing to produce a test card similar to that illustrated in FIGS. 1-6. The plastic housing (10) comprised a test window (20) that exposed the test area (140) and control area (150), as well as a buffer window (30) directly over a buffer pad. The plastic housing was also marked to indicate that the location of the test line and the control line.

The test cards were individually packaged in foil.

EXAMPLE 2

Test for HIV

Serum or plasma was prepared from a whole blood sample obtained from a patient to be tested for HIV using proper venipuncture techniques. Samples were stored at 2° C. to 8°

C. and used within 24 hours or frozen at −20° C. for use within 2 weeks. Frozen samples were thawed before use.

An HIV test card as described in Example 1, comprising a mixture of HIV-1 and HIV-2 antigens on the control area, was removed from the foil pack.

Approximately 5 µL of sample buffer comprising 0.025% HEPES and 0.2% sodium azide was applied to the membrane through the center of the test card window.

A sample pipette containing the serum or plasma to be tested was held in a vertical position over the test window on the test card and 5 µl of sample was placed onto the membrane in the center of the window.

Four drops of wash buffer solution (0.025% HEPES, 0.85% sodium chloride, 0.1% EDTA, 1% mannitol, 0.1% casein, 1% Triton X100, pH 7.2) were added to the buffer pad. After 3 minutes if the reaction was not cleared a further 1 drop of buffer was added to the buffer pad.

The results of the test were read from 1 to 5 minutes after adding the first buffer.

As shown in FIG. 5, a positive result comprises two visible lines across the sample window: a test line (140) and a control line (150). A positive result is obtained if two lines are visible, even if one of the lines is darker than the other. A negative result is indicated by a single control line visible across the sample window, as illustrated in FIG. 6.

EXAMPLE 3

HCV Test Card

A test strip for the diagnosis of hepatitis C virus was prepared as in Example 1. However, a hepatitis C antigen mixture comprising core (0.3 mg/ml), NS3 (0.4 mg/ml), and NS4 (0.1 mg/ml) was sprayed in a test line on the membrane to produce the test area, rather than HIV antigen. A total of about 0.4 µg of HCV antigen mixture was applied in the test line. Rabbit IgG diluted to 1 mg/ml was sprayed in a control line.

EXAMPLE 4

Test for HCV

An HCV test card as described in Example 3, comprising an HCV antigen on the test area, was removed from the foil pack.

Approximately 5 µL of sample buffer comprising phosphate buffer and 0.2% sodium azide was applied to the membrane through the center of the test card window.

Serum or plasma was prepared from a whole blood sample. A sample pipette containing the serum or plasma to be tested is held in a vertical position over the test window on the test card and 5 µl of sample is placed onto the membrane in the center of the window.

Four drops of wash buffer solution (0.025% phosphate, 0.85% sodium chloride, 0.1% EDTA, 1% mannitol, 0.1% casein, 1% Triton X100, pH 7.2) were added to the buffer pad. After 3 minutes if the reaction was not cleared a further 2 drops of buffer were added to the buffer pad.

The results of the test were read from 1 to 5 minutes after adding the first buffer.

As shown in FIG. 5, a positive result comprises two visible lines across the sample window: a test line (140) and a control line (150). A positive result is obtained if two lines are visible, even if one of the lines is darker than the other. A negative result is indicated by a single control line visible across the sample window, as illustrated in FIG. 6.

EXAMPLE 5

Pregnancy Test

Lateral flow rapid visual pregnancy tests are prepared. The arrangement of the test strips is essentially as illustrated in FIG. 7.

Each test strip comprises a plastic backing (6 cm×5 mm) with adhesive on both sides. The plastic backing is between about 2 mil and about 20 mil in thickness.

A test line and a control line are prepared on a nitrocellulose membrane (Millipore HF09004) by spraying with a pump dispensing system (Kinematic Automation). The test line comprises a vertical line of a antibody to human chorionic gonadotropin (hCG), preferably a monoclonal antibody. Antibodies to hCG are widely available commercially, for example from Research Diagnostics Inc. (RDI-CBL74; New Jersey, USA), Charles River Labs and other sources or may be prepared using standard procedures. A total amount of from about 0.2 to about 1 µg of antibody is applied to the test area in a vertical line.

The control line comprises a vertical line of Protein A. A total amount of protein A sufficient to produce a visible signal upon conjugate binding is applied to the control line, typically about 0.25 µg.

For each test strip, the appropriate nitrocellulose membrane is cut to a size of about 2.5 cm×5 mm and attached to the plastic backing.

A second antibody to hCG is attached to colloidal gold for the conjugate for the test. Colloidal gold-hCG antibody conjugates are available commercial, for example from Research Diagnostics Inc. Alternatively hCG antibody conjugates can be prepared using well known methods (See, e.g., U.S. Pat. No. 6,485,982, incorporated herein by reference). The conjugate is diluted in conjugate buffer to a concentration of approximately 3 OD/ml. The conjugate buffer preferably comprises 0.25% HEPES, 0.85% sodium chloride, 0.1% sodium azide, 0.1% EDTA, 0.1% casein, 1% bovine serum albumin, 1% mannitol, 5% sucrose, and 0.1% Triton X100. The buffer is adjusted to a pH of 7.2.

Conjugate is applied to a glass fiber conjugate pad (Millipore GFCP203000), which is dried and cut into 5 mm×5 mm strips.

A Whatman GF/DVA glass paper buffer pad (2 cm×5 mm) is attached to the dried conjugate pad of each test strip to serve as the buffer pad.

An absorbent pad (2 cm×5 mm) made of S&S 900 paper is attached to the end of the nitrocellulose membrane closest to the control area and a further absorbent paper (2.5 cm×5 mm; S&S 470) is attached to the absorbent pad. The absorbent paper is in turn in contact with a desiccant tablet (e.g., Tri-Sorb, Sud-Chemie), that is able to absorb a significant portion of the sample volume and thus draw sample and analyte across the test area.

Methylene blue, or another indicator, is deposited on one of the absorbent pad or absorbent paper, downstream of the test area. The movement of this volume indicator is a signal that sufficient sample has contacted the test area to allow for an accurate test.

The test strip is placed in a plastic housing to produce a test card. The plastic housing comprises a test window over the test area and control area, to allow for visualization of the test results. The housing also comprises a volume indicator window, through which movement of the volume indicator can be observed.

In some test cards, a sample cup is attached over the test window. The sample cup comprises a container for holding the sample with an outlet to allow the sample to flow to the sample application area of the test membrane through the sample window. The sample cup may also comprise a filter in the outlet. After addition of sample to the membrane, the cup is removed so that the results of the test can be seen.

In other test cards, a wick is present that protrudes from the end or side of the housing. The wick provides a path along which sample can flow to the sample application area and to the test area.

The housing also has a mechanism that allows the conjugate pad to be moved into fluid communication with the membrane.

In some test cards an ampoule containing wash buffer is also located in the housing upstream of the conjugate pad. In other test cards buffer is added to the buffer pad through a buffer window.

Activation of the mechanism moving the conjugate pad into contact with the test membrane breaks the ampoule, allowing buffer to flow to the conjugate pad. Preferably about 5 drops of wash buffer contact the conjugate pad. Activation of the mechanism also removes the sample cup or wick from the housing.

The plastic housing is marked to indicate that the location of the test line and the control line in the sample window.

EXAMPLE 6

Use of Pregnancy Test with Sample Cup

Lateral flow rapid visual pregnancy tests with a sample cup are prepared as described in Example 5.

Urine from the subject is collected and approximately 500 µl is added to a sample cup, which is attached to the test card above the sample window. When a blue color is observed in the volume indicator window the mechanism is activated bringing the conjugate pad into fluid communication with the membrane. This breaks the ampoule containing buffer and starts the test. The sample cup is removed and the results of the test are visualized in the sample window from 1 to 5 minutes later.

As shown in FIG. 5, a positive result comprises two visible lines across the sample window: a test line 140 and a control line 150. A positive result is indicated if two lines are visible, even if one of the lines is darker than the other. A negative result is indicated by a single control line 50 visible across the sample window, as illustrated in FIG. 6.

EXAMPLE 6

Use of Pregnancy Test with Wick

Lateral flow rapid visual pregnancy tests with a wick are prepared as described in Example 5.

The subject places the wick in their urine flow. A blue color observed in the volume indicator window indicates that a sufficient sample volume has contacted the test area.

A mechanism on the housing is activated bringing the conjugate pad into fluid communication with the membrane. This also breaks the ampoule containing buffer inside the housing and starts the test by causing buffer to flow to the conjugate pad. The wick is removed and the results of the test are visualized in the sample window from 1 to 5 minutes later.

As shown in FIG. 5, a positive result comprises two visible lines across the sample window: a test line 140 and a control line 150. A positive result is indicated if two lines are visible, even if one of the lines is darker than the other. A negative result is indicated by a single control line visible across the sample window, as illustrated in FIG. 6.

While the invention has been described with reference to certain preferred embodiments, it will be understood by those skilled in the art that various changes may be made and equivalents may be substituted for elements thereof without departing from the scope of the invention. In addition, many modifications may be made to adapt the teachings herein to a particular situation without departing from the essential scope of the invention. Therefore, it is intended that the invention not be limited to any particular embodiment disclosed, but that the invention will include all embodiments falling within the scope of the appended claims.

What is claimed is:

1. An immunoassay device for determining the presence of an analyte in a liquid sample, comprising:
   a buffer receiving member for receiving a buffer solution;
   a conjugate pad in moisture conductive communication with the buffer receiving member, said conjugate pad comprising,
   a composition comprising a conjugate disposed in dry state, said conjugate comprising a colored particle and a first binder capable of binding the analyte;
   a membrane strip in moisture conductive communication with the conjugate pad, the membrane strip comprising a test area located downstream of the conjugate pad, the test area comprising a second binder agent immobilized therein for forming an immobilized complex with the analyte;
   a removable porous member for receiving the liquid sample, wherein said porous member is in contact with and located directly above the test area so as to cover the test area; and wherein
   the device is configured to provide a flowpath along which the buffer solution flows into the conjugate pad to mobilize the conjugates and form a mixture comprising the buffer and the mobilized conjugates, and along which flowpath the mixture flows into the membrane strip to the test area, wherein the buffer solution of the mixture washes the immobilized complexes in the test area.

2. The device of claim 1, wherein the analyte is an antibody to immunodeficiency virus (HIV) and the second binder is selected from the group consisting of an antigen to HIV-1 and an antigen to HIV-2.

3. The device of claim 1, wherein the colored particles are colloidal gold.

4. The device of claim 3, wherein the first binder is protein A.

5. The device of claim 1, wherein the analyte is an antibody.

6. The device of claim 1, wherein the analyte is an antibody to immunodeficiency virus (HIV).

7. The device of claim 1 comprising a control area located downstream of the test area, the control area comprising an immobilized control binding agent that is able to bind the conjugate.

8. The device of claim 1 wherein the membranous strip comprises a nitrocellulose membrane.

9. The device of claim 1, wherein the porous member forms a lower wall of a container for receiving the liquid sample.

10. The device of claim 9, wherein the container is removable from the membranous strip to permit visualization of the test area.

11. The device of claim 1, wherein the porous member is filter paper.

* * * * *